United States Patent
Zlokovic et al.

(10) Patent No.: US 7,968,515 B2
(45) Date of Patent: Jun. 28, 2011

(54) PROTEIN S PROTECTS THE NERVOUS SYSTEM FROM INJURY

(75) Inventors: Berislav V. Zlokovic, Rochester, NY (US); John H. Griffin, Del Mar, CA (US)

(73) Assignees: Socratech L.L.C., Los Angeles, CA (US); The Scripps Research Institute, La Jolla, CA (US); The University of Rochester, Rochester, NY (US)

( * ) Notice: Subject to any disclaimer, the term of this patent is extended or adjusted under 35 U.S.C. 154(b) by 214 days.

(21) Appl. No.: 10/529,748

(22) PCT Filed: Sep. 30, 2003

(86) PCT No.: PCT/US03/30638
§ 371 (c)(1),
(2), (4) Date: Mar. 30, 2005

(87) PCT Pub. No.: WO2004/030619
PCT Pub. Date: Apr. 15, 2004

(65) Prior Publication Data
US 2006/0052281 A1    Mar. 9, 2006

Related U.S. Application Data

(60) Provisional application No. 60/414,333, filed on Sep. 30, 2002.

(51) Int. Cl.
*A61K 38/36* (2006.01)
(52) U.S. Cl. ...................................... 514/14.9; 514/17.7
(58) Field of Classification Search .................. None
See application file for complete search history.

(56) References Cited

U.S. PATENT DOCUMENTS

| | | | |
|---|---|---|---|
| 5,254,532 A * | 10/1993 | Schwarz et al. | 514/2 |
| 5,321,123 A | 6/1994 | Griffin et al. | |
| 5,405,946 A | 4/1995 | Griffin et al. | |
| 5,656,484 A | 8/1997 | Bouma et al. | |
| 5,663,142 A | 9/1997 | Bouma et al. | |
| 5,804,181 A | 9/1998 | Eibl et al. | |
| 5,891,843 A | 4/1999 | Turecek et al. | |
| 6,379,975 B1 | 4/2002 | Linse et al. | |
| 7,074,402 B2 * | 7/2006 | Griffin et al. | 424/94.64 |
| 2002/0028199 A1 | 3/2002 | Griffin et al. | |
| 2003/0060415 A1* | 3/2003 | Hung | 514/12 |
| 2003/0165485 A1* | 9/2003 | Bertilsson et al. | 424/94.6 |
| 2006/0052281 A1 | 3/2006 | Zlokovic et al. | |
| 2007/0142272 A1 | 6/2007 | Zlokovic et al. | |

FOREIGN PATENT DOCUMENTS

| | | |
|---|---|---|
| WO | 01/56532 A2 | 8/2001 |
| WO | 2004/030619 A2 | 4/2004 |
| WO | 2004/056309 A2 | 7/2004 |
| WO | 2004/030619 A3 | 6/2005 |

OTHER PUBLICATIONS

Rudinger, In "Peptide Hormones" (ed., J.A. Parsons) University Park Press, Baltimore, pp. 1-7 (1976).*
Honig 1999. Journal of Molecular Biology 293:283-293.*
Lan et al. 2000 Blood 95:633-638.*
Cheng et al. "Neuroprotective and anti-thrombotic effects of protein S in a murine model of stroke" Soc. Neurosci. Abstract No. 390.13, 2002.
Int'l Search Report dated Apr. 18, 2005 for PCT/US2003/030638.
Benzakour et al. "The anticoagulant factor, protein S, is produced by cultured human vascular smooth muscle cells and its expression is up-regulated by thrombin" Blood 95:2008-2014 (2000).
Cheng et al. "Activated protein C blocks p53-mediated apoptosis in ischemic human brain endothelium and is neuroprotective" Nature Med. 9:338-342 (2003).
Cheng et al. "Activated protein C inhibits tissue plasminogen activator-induced brain hemorrhage" Nature Med. 12:1278-1285 (2006).
Dömötör et al. "Activated protein C alters cytosolic calcium flux in human brain endothelium via binding to endothelial protein C receptor and activation of protease activated receptor-1" Blood 101:4797-4801 (2003).
Gandrille et al. "Protein S deficiency: A database of mutations—First update" Thromb. Haemost. 84:918-944 (2000).
Guo et al. "Activated protein C prevents neuronal apoptosis via protease activated receptors 1 and 3" Neuron 41:563-572 (2004).
Liu et al. "Protein S confers neuronal protection during ischemic/hypoxic injury in mice" Circulation 107:1791-1796 (2003).
Shibata et al. "Anti-inflammatory, antithrombotic, and neuroprotective effects of activated protein C in a murine model of focal ischemic stroke" Circulation 103:1799-1805 (2001).
Eby "Prothrombotic states in ischemic stroke" Sem. Cerebrovascular Dis. Stroke 2:90-101 (2002).
Simioni et al. "Childhood stroke associated with familial protein S deficiency" Brain & Devel. 16:241-245 (1994).

(Continued)

*Primary Examiner* — Daniel E Kolker
(74) *Attorney, Agent, or Firm* — Nixon & Vanderhye P.C.

(57) ABSTRACT

Protein S is a significant neuroprotectant when administered after focal ischemic stroke and prevents hypoxic/re-oxygenation injury. Purified human plasma-derived or recombinant protein S improves motor neurological function after stroke, and reduced brain infarction and edema. Protein S also enhances post-ischemic reperfusion and reduced brain fibrin and neutrophil deposition. Cortical neurons are protected from hypoxia/re-oxygenation-induced apoptosis. Thus, protein S and variants thereof are prototypes of a class of agents for preventing injury of the nervous system. In particular, a disease or other pathological condition (e.g., stroke) may be treated with such agents having one or more protein S activities (e.g., anti-thrombotic and anti-inflammatory activities, direct cellular neuronal protective effects) although the latter activities are not be required.

9 Claims, 5 Drawing Sheets

OTHER PUBLICATIONS

Figure 3A:
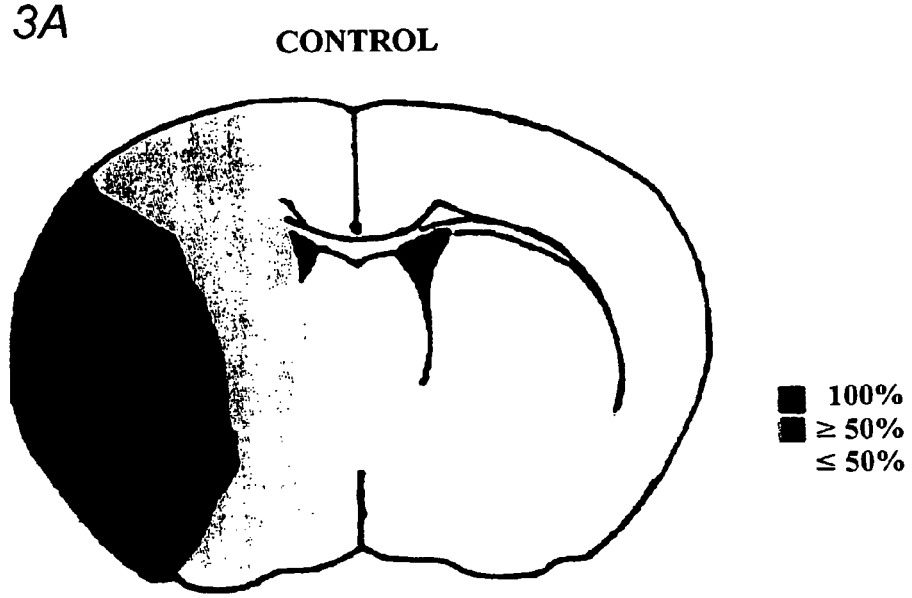

Webb et al. "Vitamin K-dependent protein S localizing complement regulator C4b-binding protein to the surface of apoptotic cells" J. Immunol. 169:2580-2586 (2002).

Supplementary Search Report for European Appln. No. 03799306.0 dated Jun. 10, 2008.

Chen et al. "Statins induce angiogenesis, neurogenesis, and synaptogenesis after stroke" Ann. Neurol. 53:743-751 (2003).

Godowski et al. "Reevaluation of the roles of protein S and Gas6 as ligands for the receptor tyrosine kinase Rse/Tyro 3" Cell 82:355-358 (1995).

Nagata et al. "Identification of the product of growth arrest-specific gene 6 as a common ligand for Axl, Sky and Mer receptor tyrosine kinases" J. Biol. Chem. 47:30022-30027 (1996).

Ohashi et al. "Stimulation of sky receptor tyrosine kinase by the product of growth arrest-specific Gene 6" J. Biol. Chem. 270:22681-22684 (1995).

Wang et al. "Treatment of stroke with erythropoietin enhances neurogenesis and angiogenesis and improves neurological function in rats" Stroke 35:1732-1737 (2004).

Zhang et al. "Sildenafil (Viagra) induces neurogenesis and promotes functional recovery after stroke in rats" Stroke 33:2675-2680 (2002).

* cited by examiner

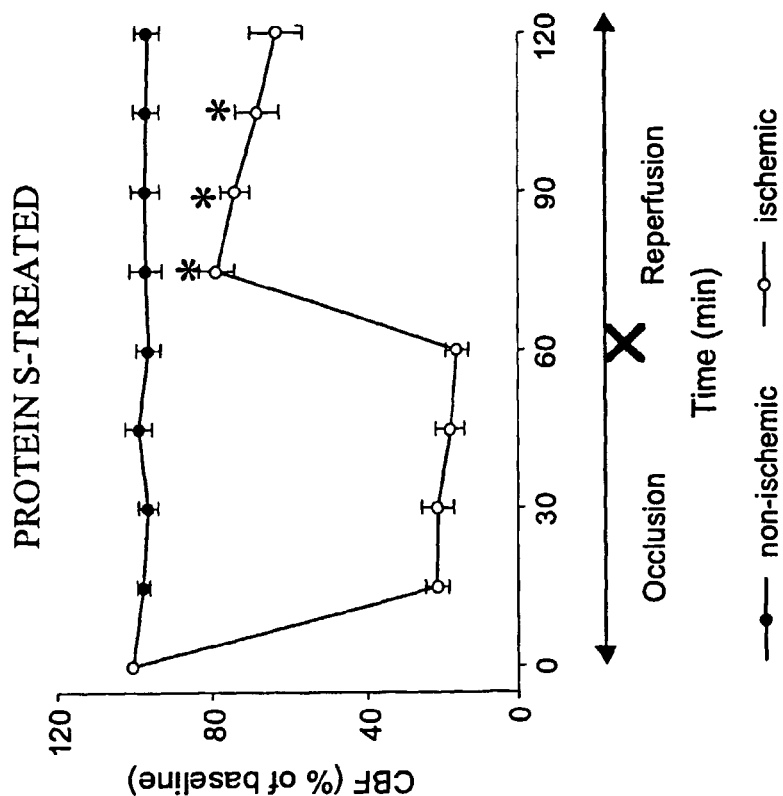
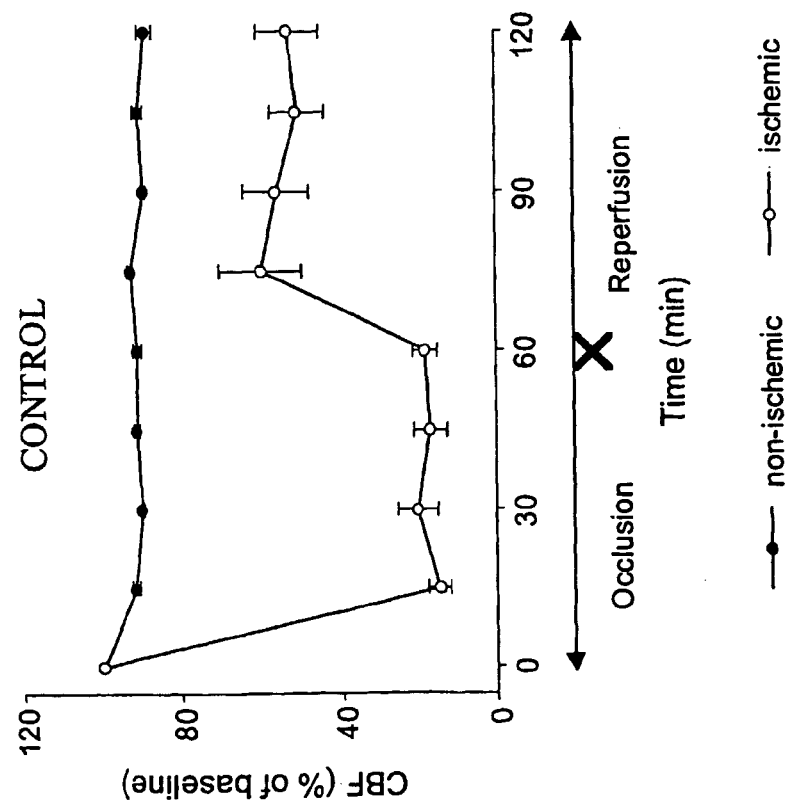
Figure 1B
Figure 1A

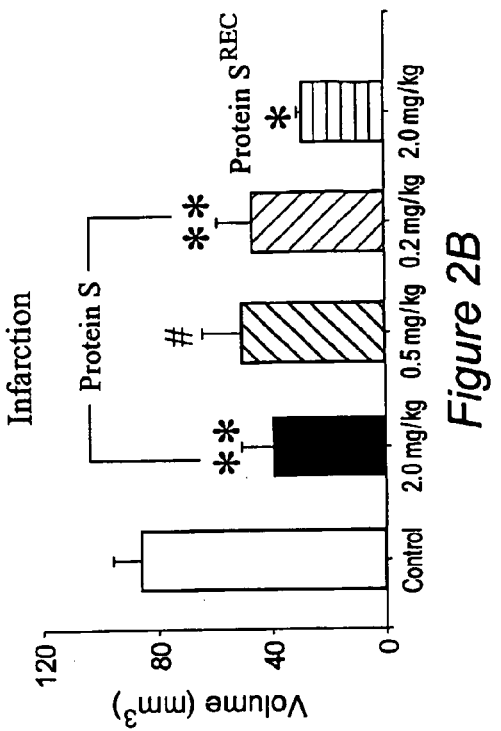
*Figure 2A*
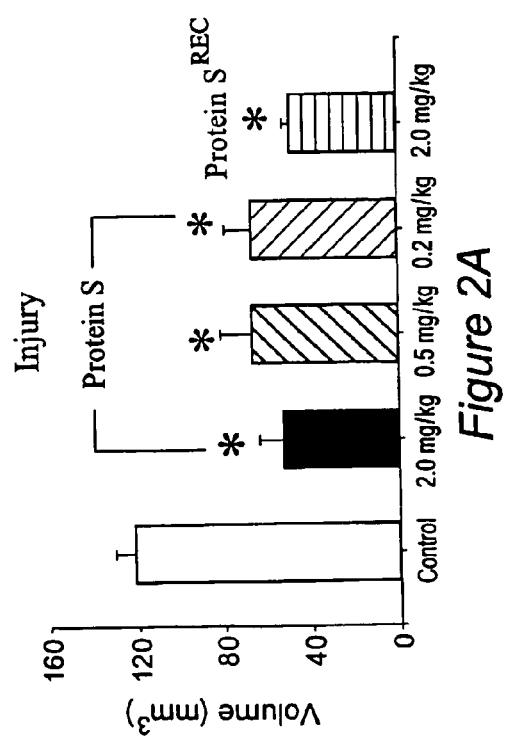
*Figure 2C*
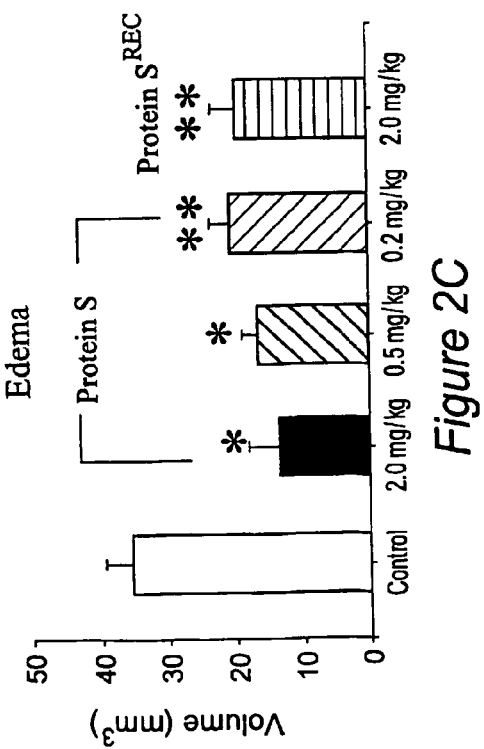
*Figure 2B*
*Figure 2D*

CONTROL

■ 100%
▨ ≥ 50%
  ≤ 50%

PROTEIN S-TREATED

PROTEIN S PROTECTS THE NERVOUS SYSTEM FROM INJURY

CROSS-REFERENCE TO RELATED APPLICATIONS

This application is a national phase application of International Patent Appln. No. PCT/US2003/030638, filed Sep. 30, 2003; which claims the benefit of provisional Appln. No. 60/414,333, filed Sep. 30, 2002; which is incorporated by reference herein.

FEDERALLY-SPONSORED RESEARCH OR DEVELOPMENT

The U.S. Government has certain rights in this invention as provided by NIH grants HL63290 and HL21544 from the Department of Health and Human Services.

BACKGROUND OF THE INVENTION

This invention relates to the use of protein S and/or variants thereof as neuroprotective agents for treating brain disorders and other pathological conditions. The ability of protein S and variants thereof to act as cell survival factors on cells of the nervous systems are demonstrated.

Benzakour and Kanthou (*Blood* 95:2008-2014, 2000) showed that protein S is produced by smooth muscle cells derived from abdominal arteries. They suggested that protein S may be an important autocrine factor in the pathophysiology of the vasculature by acting as a mitogen for these cells. In more recent work, they induced apoptosis of abdominal vessel, smooth muscle cells using sodium nitroprusside or hydrogen peroxide. Pre-treatment with protein S reduced apoptosis and cell death (Kanthou & Benzakour in *Angiogenesis: From the Molecular to Integrative Pharmacology*, pp. 155-166, 2000).

These studies did not address the role of protein S in the nervous system or, more specifically, its effects on brain endothelial cells.

The present invention addresses the need for neuroprotective compositions and methods for their use to treat diseases associated with a variety of types of nervous system damage, thrombosis, and inflammation. Because injury usually occurs after a triggering event, treatment may be initiated after such an event.

Therefore, it is an objective of the invention to show how to use protein S and variants thereof as neuroprotective agents. A long-felt need for new therapeutic and prophylactic compositions is addressed thereby. Also provided are compositions that have been formulated to deliver protein S or variants thereof to the central nervous system and processes for using and making the aforementioned products. Further objectives and advantages of the invention are described below.

SUMMARY OF THE INVENTION

The present invention is directed to improved protection of cells of the nervous system. An effective amount of protein S or at least one variant thereof may be used. It may or may not have one or more optional activities: for example, inhibition of any combination of cellular stress, apoptosis, injury, or cell death; prevention of cell injury or tissue damage caused by ischemia, hypoxia, re-oxygenation, reperfusion, or the like; and anti-thrombotic and/or anti-inflammatory activity.

The subject in need of treatment may be at risk for or already affected by the disease or other pathological condition. Treatment may be initiated before and/or after diagnosis. An indication that treatment is effective may be increased function or improved neurological outcome including improved motor neurological performance, improved performance on psychiatric tests, improved level of cognitive performance; decreased brain damage due to head injury, ischemic injury, infarction, edema, or a combination thereof; decreased injury of the nervous system; or increased cerebral blood flow. Increase or decrease may be determined by comparison to treatment without protein S or variant thereof, or to the expected effects of untreated disease or another pathological condition. Other advantages and improvements are discussed below or would be apparent from the disclosure herein.

Therefore, the invention provides a treatment for therapy or prophylaxis and the products used therein. Pharmaceutical compositions may be manufactured and assessed in accordance therewith. Further aspects of the invention will be apparent to persons skilled in the art from the following detailed description and claims, and generalizations thereto.

BRIEF DESCRIPTIONS OF THE DRAWINGS

FIGS. 1A-1B show cerebral blood flow (CBF) during middle cerebral artery (MCA) occlusion/reperfusion in control (FIG. 1A) and protein S-treated mice (FIG. 1B). Vehicle or protein S (2 mg/kg) was given 10 min after initiation of the MCA occlusion. CBF values (mean ±SD) in the ischemic (open symbols) and non-ischemic hemisphere (closed symbols) in six controls and six protein S-treated mice were measured. *$p<0.05$ between the two groups.

FIGS. 2A-2D show brain injury in control and protein S-treated mice. FIGS. 2A to 2C: The volumes of brain injury, infarction and edema (mean ±SE) from control mice (n=6); mice treated with human plasma-derived protein S at 0.2 mg/kg (n=5), 0.5 mg/kg (n=6) or 2 mg/kg (n=6); and mice treated with recombinant protein $S^{REC}$ at 2 mg/kg (n=4); *$p<0.01$, **$p<0.05$, #$p=0.059$. FIG. 2D: Infarct area in the seven coronal sections from the brains of control mice and mice treated with 0.5 mg/kg protein S (mean ±SE); * $p<0.05$. Vehicle or protein S was given 10 min after initiation of MCA occlusion.

Figure 3B:
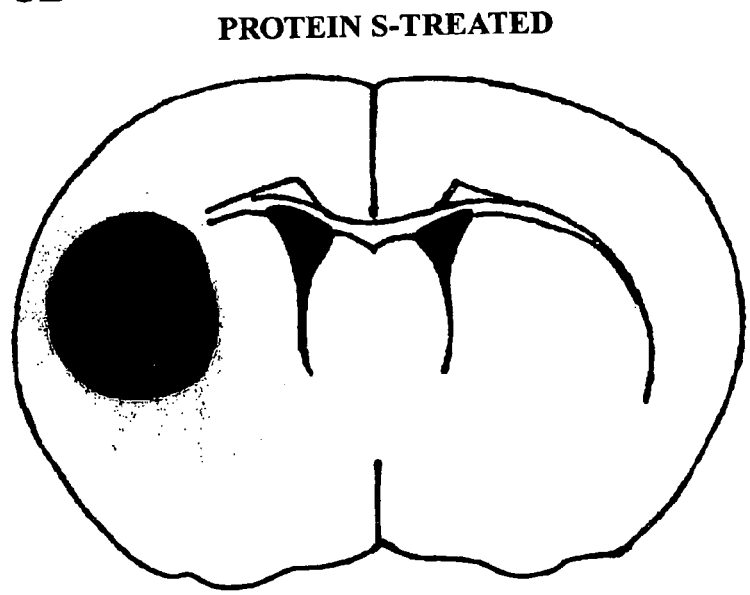

FIGS. 3A-3B show the incidence and topography of the infarction at the level of the optic chiasm in control mice (FIG. 3A) and mice receiving plasma-derived protein S (FIG. 3B). Key for the incidence is given in FIG. 3A. Vehicle (n=6) or protein S (2 mg/kg, n=6) was given 10 min after initiation of MCA occlusion.

Figure 4A:
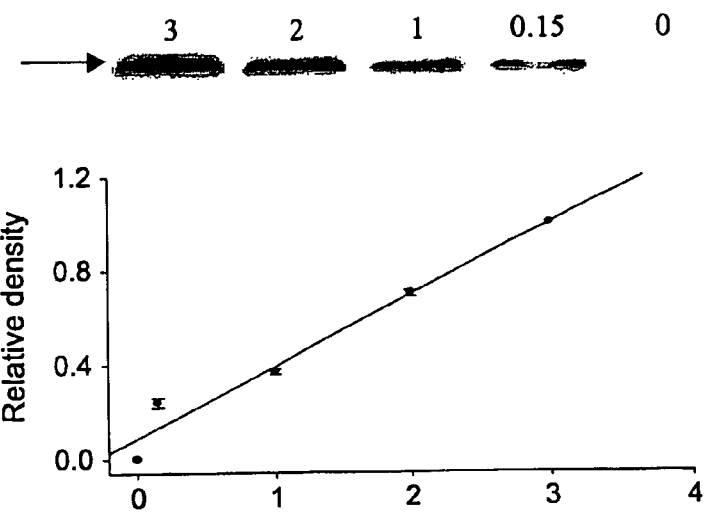
Figure 4B:
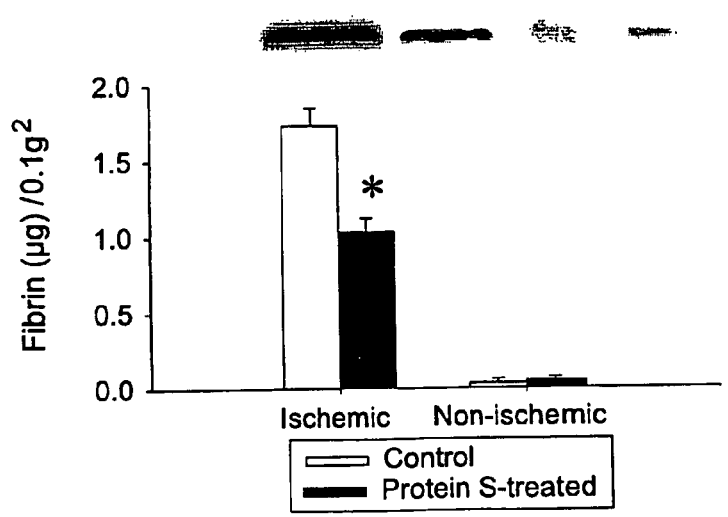
Figure 4C:
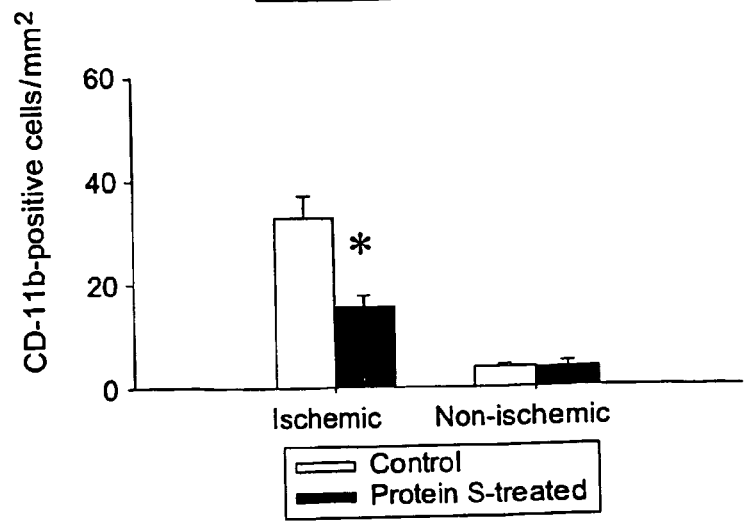

FIGS. 4A-4C show deposition of fibrin at the level of optic chiasm and CD11b-positive leukocytes in the ischemic and non-ischemic hemispheres in control mice and protein S-treated (2 mg/kg) mice. FIG. 4A: Signal on Western blot for fibrin from the standard curve was linear between 0.15 and 3 µg of fibrin β-chain/0.1 ml; 3 µg/0.1 ml was arbitrarily set as 1 unit. FIG. 4B: Western blot analysis of 10 mg brain homogenate (mean±SE) in control (n=3) and protein S-treated mice (n=3). FIG. 4C: CD11b-positive leukocytes (mean±SE) from six controls (open bars) and six protein S-treated mice (closed bars). *$p<0.05$.

Figure 5B:
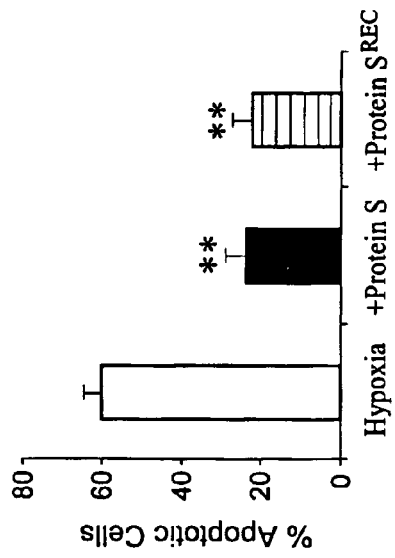
Figure 5D:
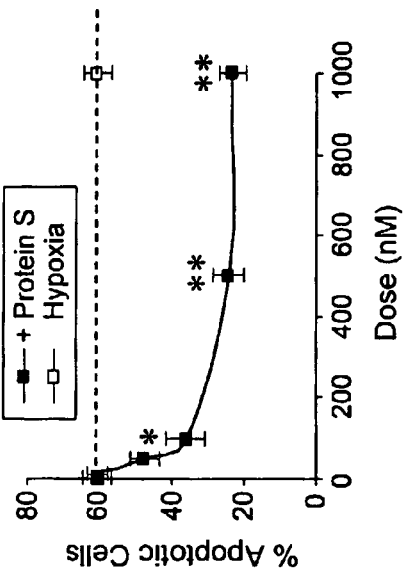
Figure 5A:
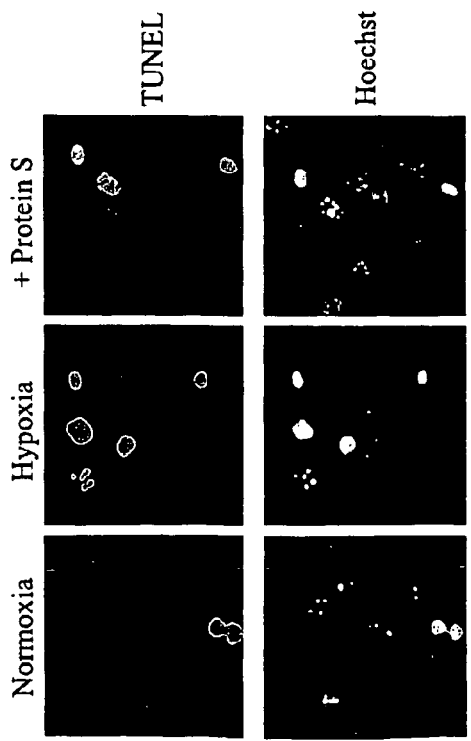
Figure 5C:
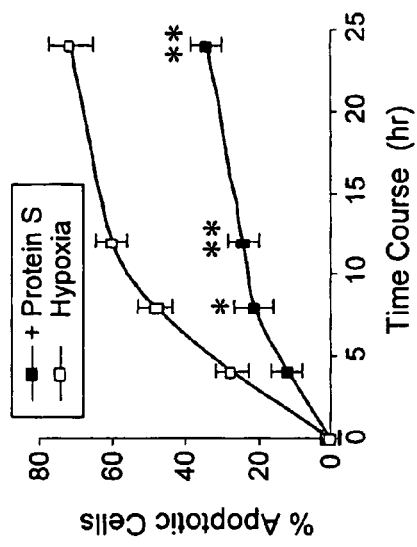

FIGS. 5A-5D show neuroprotective effects of protein S in cultured mouse cortical neurons subjected for 12 hr to hypoxia/aglycemia followed by 12 hr re-oxygenation. FIG. 5A: TUNEL-positive neurons (upper) and neurons showing chromatin condensation and/or nuclear fragmentation by Hoechst staining (lower) under normoxic conditions (left), hypoxia/re-oxygenation (middle) and hypoxia/re-oxygenation with protein S (500 nM, right). FIG. 5B: TUNEL-positive neurons in the absence or presence of protein S or recombinant protein $S^{REC}$ corrected for basal values of apoptosis. FIG. 5C: Time-course for anti-apoptotic effect of protein S. FIG. 5D: Dose-response for neuroprotective effect of protein S. Hypoxia/re-oxygenation in the absence (open squares) or presence of increasing concentrations of protein S (solid squares). Mean±SE, from 3 to 5 cultures. *p<0.05 and **p<0.01.

DESCRIPTION OF SPECIFIC EMBODIMENTS OF THE INVENTION

Protein S is a physiologic anti-thrombotic agent that inhibits prothrom-binase complex activity on endothelial cells and platelets by inhibiting coagulation factors Va and Xa. Protein S is also a cofactor for activated protein C, a serine protease that inactivates coagulation factors Va and VIIIa (1-7). The critical physiologic anti-thrombotic role of protein S is revealed by the massive thrombotic complications suffered by infants homozygous for protein S deficiency (8,9). In adults, mild heterozygous deficiencies in protein S are reported to be associated with a risk for venous and arterial thrombosis (10-13), ischemic stroke (14,15), and cerebral thrombophlebitis (16,17).

In addition to its anticoagulant activity, protein S binds to vascular cells and is a potent mitogen (18-20). A structural homolog of protein S, the growth arrest specific gene-6 (gas6), is a survival factor (21). Gas6 rescues cells from apoptosis induced by serum withdrawal (22-24). It has been suggested that both protein S and gas6 are ligands for the Tyro3/Axl family of receptor tyrosine kinases (25). But the extent to which protein S functions in vivo as a ligand for Tyro3/Axl receptors was unclear (26) until the present results were obtained.

Ischemic strokes in humans are due to thrombotic or thromboembolic vascular occlusions (27) resulting in post-ischemic neurodegenerative disorder. Protein S had significant anti-thrombotic activity in a rabbit model of peripheral arterial thrombosis (28), but its potential for stroke therapy has not been explored. In contrast to a fibrinolytic agent, e.g., tissue plasminogen activator (tPA) which may predispose to CNS bleeding (29) and is neurotoxic (30,31), elevated levels of bovine protein S in rabbits did not cause bleeding (28). No neuroprotection was observed.

We determined whether protein S may control ischemic brain damage by protecting cells of the brain (e.g., neurons, brain endothelial cells, vascular smooth muscle cells of brain vasculature, pericytes, astrocytes, microglia, oligodendrocytes, and stems cells including neuronal or oligodendrocyte precursors) from ischemic/hypoxic injury; promoting anticoagulation; controlling cerebrovascular thrombosis; or combinations thereof.

Hereditary protein S deficiency is an autosomal dominant disorder that is associated with a risk of recurrent and inappropriate clot formation. Most likely consequences are venous thrombosis and pulmonary embolism, but protein S deficiency may also predispose patients to arterial thrombotic disease. Few homozygous or compound heterozygous subjects have been reported. Such a genotype may be incompatible with survival to adulthood without treatment because of the development of severe purpura fulminans shortly after birth.

While protein S deficiency in the general population is relatively rare (up to a few percent), it is found in up to 10% of young patients with venous thrombosis. Many other circumstances may lead to acquired protein S deficiency such as oral anticoagulant therapy, oral contraception, liver disease, nephrotic syndrome, disseminated intravascular coagulation, and pregnancy. Other factors that affect protein S activity are gender (women have a lower protein S level than men) and age (total protein S level increases with age in women due to their hormonal status). Total and free protein S levels are also positively correlated with triglyceride and cholesterol levels.

In neurodegenerative diseases, neuronal cells degenerate to bring about deterioration of cognitive function. A variety of diseases and neurological deficiencies may bring about such degeneration including Alzheimer's disease, Huntington disease or chorea, hypoxia or ischemia caused by stroke, cell death caused by epilepsy, amyotrophic lateral sclerosis, mental retardation and the like, as well as neurodegenerative changes resulting from aging.

The neuroprotective activity of protein S and its functional variants may also be obtained by increasing its biological activity (e.g., gene therapy, gene activation), decreasing the biological activity of an inhibitor (e.g., reducing C4b binding protein amount or activity), and other methods of altering protein S activity.

The present invention is useful for treating many clinical conditions involving inflammatory processes. For example, inflammatory bowel disease including Crohn's disease and ulcerative colitis are spontaneous chronic inflammations of the gastrointestinal tract which involve activation of inflammatory cells whose products cause tissue injury. Neutrophils, eosinophils, mast cells, lymphocytes, and macrophages may contribute to the inflammatory response.

The present invention is also directed to treatment of systemic shock and many resultant clinical conditions associated therewith. Systemic shock often occurs as a complication of severe blood loss, severe localized bacterial infection, or ischemia/reperfusion trauma and it is a major cause of death in intensive care units. Many cases of septic shock are induced by endotoxins (i.e., lipopolysaccharides or LPS) from gram negative bacilli or toxins (i.e., toxic shock toxin 1) from gram-positive cocci bacteria. The release of LPS in the bloodstream causes release of inflammatory mediators (e.g., cytokines, platelet activating factor, complement, leukotrienes, oxygen metabolites, and the like) which cause myocardial dysfunction, vasodilation, hypotension, endothelial injury, leukocyte adhesion and aggregation, disseminated intravascular coagulation, adult respiratory distress syndrome (ARDS), or failure of liver, kidney, or central nervous system (CNS). Shock due to blood loss also involves inflammatory mediator release. In each case, inflammatory responses are induced at the original site of trauma, and also in the vasculature and remote vascularized sites.

Myocardial ischemia is associated with activation of the complement system which further promotes cardiac injury with the enhancement of a series of inflammatory events. Life threatening local and remote tissue damage occurs during surgery, trauma, and stroke when major vascular beds are deprived for a time of oxygenation (ischemia) then restored with normal circulation (reperfusion). Reperfusion injury is characterized by vascular permeability leading to edema and infiltration of inflammatory cells. Neutrophils contribute significantly to reperfusion damage by generating oxidants or releasing proteases that damage the microvasculature or adjacent tissue. Cell death and tissue damage due to complement and inflammatory cell mechanisms lead to organ failure or decreased organ function. The activation of mediators by a local injury can also cause a remote injury to highly vascularized organs. The compositions and methodologies of the present invention are useful in the treatment of such injury.

Inflammatory response damage also occurs in glomerulonephritis as well as tubule disease. Infiltration of inflammatory cells (especially macrophages) is linked to proteinuria accompanied histologically by hypercellularity and crescent formation in glomeruli. Over a longer term, the infiltration of inflammatory cells is associated with accumulation of extracellular matrix and sclerosis and chronic compromise of renal function. The present invention is also efficacious in treating glomerulonephritis and tubule disease.

There are many other disease and pathological conditions which benefit from the methodologies of the present invention such as for example, coronary arterial occlusion, cardiac arrhythmias, congestive heart failure, cardiomyopathy, bronchitis, acute allergic reactions and hypersensitivity, neurotrauma, graft/transplant rejection, myocarditis, insulin dependent diabetes, and stroke. Stroke involves a very strong inflammatory response, that in part may be responsible for neuronal damage directly by allowing leukocytes to enter the extravascular regions of the brain and destroy normal brain cells and neurons, and indirectly by obstructing microvessels and stopping blood flow due to the procoagulant effects of inflammation. These intravascular and extravascular processes may require adhesion molecules and cytokines that are direct or indirect targets of cellular interactions which are independent of anticoagulant effects.

In addition to treating patients suffering from the trauma resulting from heart attack, patients suffering from actual physical trauma could be treated in order to relieve the amount of inflammation and swelling which normally result after an area of the body is subjected to severe trauma. Also, patients suffering from hemorrhagic shock could be treated to alleviate inflammation associated with restoring blood flow. Other disease states which might be treated using formulations of the invention include various types of arthritis, various chronic inflammatory conditions of the skin, insulin-dependent diabetes, and adult respiratory distress syndrome. After reading the present disclosure, those skilled in the art will recognize other disease states and/or symptoms which might be treated and/or mitigated by the present invention.

Some examples of arterial thrombosis where protein S alone or in combination with a thrombolytic agent, anticoagulant, anti-platelet agent, or anti-inflammatory agent is useful include the following clinical settings: i) acute arterial thrombotic occlusion including coronary, cerebral, or peripheral arteries; ii) thrombotic occlusion or restenosis after angioplasty; iii) reocclusion or restenosis after thrombolytic therapy; and iv) venous thrombotic occlusion. Thrombolytic agents such as t-PA salvage ischerhic tissue when used within hours of acute heart attack or stroke by re-establishing blood flow in the occluded artery. Between one-fourth and one-third of patients who have successful thrombolytic reperfusion of occluded coronary arteries subsequently undergo reocclusion after discontinuing t-PA infusion. This complication occurs despite full-dose heparin therapy. The present invention may have greater efficacy than heparin in preventing reocclusion. Problems with thrombolytic therapy with t-PA include neurotoxicity and killing of neurons. The addition of protein S might reduce or prevent such unwanted consequences. v) Small and large caliber vascular graft occlusion. Vascular grafts of small caliber, i.e., 3-/mm diameter, have a high frequency of thrombotic occlusion. Protein S alone or in combination with a thrombolytic agent is useful to prevent occlusion. vi) Hemodialysis. The prosthetic surfaces and flow design of all hemodialyzers are thrombogenic. Currently heparin is infused during dialysis. However, heparin is only partially effective, thereby limiting the reuse of dialyzers. Also, heparin has a number of troublesome side effects and complications. vii) Cardiopulmonary bypass surgery. To prevent thrombus formation in the oxygenator and pump apparatus, heparin is currently used. However, it fails to inhibit platelet activation and the resultant transient platelet dysfunction which predisposes to bleeding problems post-operatively. viii) Left ventricular cardiac assist device. This prosthetic pump is highly thrombogenic and results in life threatening thromboembolic events—complications that are only partially reduced by conventional anticoagulants (heparin or coumarin drugs). ix) Total artificial heart and left ventricular assist devices. x) Other arterial thrombosis. Protein S is useful for arterial thrombosis or thromboembolism where current therapeutic measures are either contraindicated or not effective. For example, protein S is useful for treating acute pre-or post-capillary occlusion, including transplantation, retinal thrombosis, or microthrombotic necrosis of any organ complicating infections, tumors, or coumarin treatment.

In another embodiment, the present invention provides methods for protecting cells of the nervous system from cell death in a subject having or at risk of disease or another pathological condition. The method includes administering an effective amount of protein S to the subject to provide neuroprotection. Examples of such disorders include, but are not limited to, stroke, Alzheimer's disease, Huntington disease, ischemia, epilepsy, amyotrophic lateral sclerosis, mental retardation and aging. One "having or at risk of having" an inflammatory vascular disease as described herein is a subject either exhibiting symptoms of the disease or diagnosed as being at risk for developing the disease. Such subjects include those having undergone or preparing for surgical procedures as described below.

In yet another embodiment, the invention provides methods for reducing inflammation in a subject having or at risk of having a neuropathological disorder. The method includes administering an anti-inflammatory effective amount of protein S to the subject, thereby reducing neurological inflammation in the subject. The methodologies of the present invention may also be efficacious in treating multiple sclerosis (MS) in addition to neuropathologies described above. MS is often characterized by the penetration of the blood-brain barrier by circulating leukocytes, leading to demyelination in various parts of the brain, impaired nerve conduction and, ultimately, paralysis.

The term "neuroprotective" is used to denote protection of any type of cell of the nervous system including neurons, brain endothelial cells, brain vascular smooth muscle cells, pericytes, astrocytes, oligodendrocytes, stem cells including neuronal and oligodendrocyte precursors, and microglia from cellular stress, injury, and/or cell death, including ischemia and hypoxia.

The term "neurodegenerative disease" is used to denote conditions which result from loss of neurons, neuronal cell injury or loss, and/or injury of other types of brain cells such as oligodendrocytes or brain endothelial cells and/or other vascular cells, but not limited to any cell type in the nervous system which may bring about deterioration of motor or sensory functions of the nervous system, cognitive function, higher integrative intellectual functions, memory, vision, hearing etc. Such degeneration of neural cells may be caused by Alzheimer's disease characterized by synaptic loss and loss of neurons; Huntington disease or chorea; by pathological conditions caused by temporary lack of blood or oxygen supply to the brain, e.g., brought about by stroke; by epileptic seizures; due to chronic conditions such as amyotrophic lateral sclerosis, mental retardation; as well as due to normal degeneration due to aging. It should be noted that diseases such as stroke and Alzheimer's have both a neurodegenerative and an inflammatory vascular component and thus are treated by the methods of the invention.

One aspect of the invention includes the neuroprotective activity of protein S. The term "neuron" includes hundreds of different types of neurons, each with distinct properties. Each type of neuron produces and responds to different combinations of neurotransmitters and neurotrophic factors. Neurons are thought not to divide in the adult brain, nor do they generally survive long in vitro. The method of the invention provides for the protection from cell death or injury of neurons from virtually any region of the brain and spinal cord. Neurons include those in embryonic, fetal or adult neural tissue, including tissue from the hippocampus, cerebellum, spinal cord, cortex (e.g., motor or somatosensory cortex), striatum, basal forebrain (e.g., cholenergic neurons), ventral mesence-phalon (e.g., cells of the substantia nigra), and the locus ceruleus (e.g., neuro-adrenaline cells of the central nervous system).

Genetics and Structure of Protein S

The human genome contains two genes: PROS1 is functional and encodes protein S and PROS2 is a pseudogene. Both genes are located on chromosome 3 at 3p11.1-3q11.2 and are linked within 4 cM. The PROS1 gene occupies about 80 kb of DNA with 15 exons. PROS1 and PROS2 are 97% and 95% identical between corresponding exons and introns, respectively. PROS2 lacks exon 1 and contains multiple base changes in the coding portions with termination codons at amino acid residues 61, 299, 410 and 522 a frameshift mutation in exon 10. Three mRNA species are transcribed from PROS1 and then translated into human protein S. The major mRNA species is about 4 kb. Three frequent polymorphisms have been described in the protein S gene: the first is located in the coding region (Pro 626 encoded either by CCA or by CCG) and the other two are located in noncoding regions (a C to T transition in intron 5 which is four bases downstream of exon 11, and a C to A transversion which is 520 bases downstream of the Stop codon).

The intron-exon organization of the gene for protein S reflects its modular structure. The first eight exons encode structural/functional domains also found in other vitamin K-dependent coagulation proteins (except for exon IV, coding for the thrombin-sensitive loop) and have been placed upstream of the ancestral gene of a steroid hormone binding protein. The 3' part of exon 1 codes for the signal peptide, exon 2 for the propeptide and the GLA-domain, exon 3 for the helical stack domain, exon 4 for the thrombin-sensitive loop, exons 5 to 8 for four epi-dermal growth factor-like domains, and exons 9 to 14 and the first 161 bp of exon 15 for the sex hormone-binding globulin-homologous domain. At least partial sequences for protein S from human, monkey, mouse, rat, rabbit and cow are known. After alignment, they are about 59% identical at the amino acid level.

The plasma concentration of protein S is about 25 mg/L (about 0.33 µM). The protein functions as a non-enzymatic cofactor to activated protein C (APC) in the proteolytic degradation of factors Va and VIIIa. Protein S increases 10-fold the affinity of APC for negatively charged phospholipids. The two proteins form a putative 1:1 complex on lipid surfaces such as platelets. Protein S has a direct APC-independent anticoagulant activity by inhibition of prothrombinase activity and of factor X activating complex by binding to factor VIII. The importance of these properties in physiological anticoagulant mechanisms remains to be demonstrated. Protein S circulates in human plasma in two forms: about 40% free and about 60% bound to a regulator of the classical complement pathway, C4b-BP. Only the free protein S (about 120 nM) has cofactor activity for APC. The plasma concentration of C4b-BP is about 150 mg/L (about 0.26 µM). Interaction between protein S and C4b-BP is non-covalent and reversible. Protein S interacts with the β-chain of C4b-BP while the α-chains of C4b-BP are devoted to binding the complement protein C4b. Thus, only C4b-BP isoforms containing a β-chain (representing about 80% of circulating C4b-BP) are able to bind protein S. In the presence of calcium ions, the dissociation constant is approximately $5 \times 10^{-10}$ M and all β-chain containing C4b-BP is linked to protein S. In healthy individuals, the concentration of free protein S is largely determined by the concentration of C4b-BPβ+ and corresponds to the molar excess of protein S over C4b-BPβ+.

Protein S in its mature form is a single-chain glycoprotein of 635 amino acids resulting from post-translational modification of a 676 amino acid precursor. It has three glycosylation sites (Asn 458, 468 and 489) and seven domains with different functional or structural roles. The signal peptide (residues −41 to −18) inserts into the rough endoplasmic reticulum and drives membrane translocation; the propeptide (residues −17 to −1) is necessary for carboxylase recognition and γ-carboxylation. These two domains are released by a cleavage reaction before secretion. The mature N-terminal part of the protein is composed of a GLA-domain (residues 1 to 37) containing 11 γ-carboxyglutamic acids which bind multiple calcium ions. The resulting stabilized structure has a high affinity for negatively-charged phospholipid membranes. The GLA-domain is followed by a short helical stack (residues 38 to 45) with a relatively high content of aromatic residues.

Whereas the above domains are present in all vitamin K-dependent proteins, the thrombin-sensitive region (residues 46 to 72) is found only in protein S. This domain contains two Cys residues (47 and 72) linked by a disulfide loop in which three peptide bonds are sensitive to thrombin proteolysis and it has recently been shown that circulating cleaved protein S is cleaved after Arg60, a site already described as sensitive to factor Xa cleavage. Whatever enzyme is responsible for the in vivo cleavage of protein S, the GLA-domain remains linked to the rest of the molecule by the disulfide bond. Since the GLA domain can no longer adopt the calcium-dependent conformation required for biological activity, protein S cannot bind to phospholipids at physiological calcium ion concentration and APC cofactor activity is lost. Therefore, this mutation may be used to separate APC cofactor activity from other activities of protein S (e.g., neuroprotective activity). These findings also suggest that the thrombin-sensitive loop interacts with APC and is involved in GLA-domain folding. Four epidermal growth factor-like domains (residues 76 to 242) are adjacent to the thrombin-sensitive region. EGF1 contains a β-hydroxy-lated Asp residue while the other three contain β-hydroxylated Asn. The EGF domains contain high-affinity calcium ion binding sites. The carboxy-terminal half of protein S is a large module homologous to sex hormone binding globulin. It contains two small disulfide loops formed by internal disulfide bonds. This module does not bind steroids, but contains at least two potential interaction sites with C4b-BP: residues 420 to 433 and residues 583 to 635.

Mutations in the protein S gene may be classified as qualitative or quantitative. A qualitative deficiency (type II) results in decrease protein S activity associated with normal levels of total or free protein S. Quantitative deficiencies have reductions in both total and free protein S (type I) or only free protein S (type III).

Frameshift mutations included 27 different insertions or deletions smaller than seven bases. Assay of protein S in plasma showed type I deficiency. Other quantitative defects resulted from insertions, deletions, splice site mutations, frameshift mutations, and missense mutations. Only seven different nucleotide substitutions are known to be responsible for type II deficiency. Five are missense mutations (Arg-2Leu, Arg-1His, Lys9Glu, Thr103Asn, Lys155Glu) with three being located in the pro-peptide or the GLA domain. The plasma phenotype of the patient with the Thr103Asn mutation supports the role of this amino acid in the interaction with APC. Two splice site mutations were also associated with type II deficiency. One activated a cryptic splice site (intron g, AT, exon 8-2) and results in a deletion of two amino acids from the protein (Ile-Asp 203-204). The other resulted in two alternative splice transcripts, lacking either exon 5 or both exons 5 and 6. An EGF1-lacking protein S species, corresponding to the exon 5-lacking transcript, was detected in the patient's plasma.

Three frequent polymorphisms and 18 rare polymorphisms do not appear to have an effect on protein S activity. They include missense changes (Pro35Leu, Arg192Lys, Thr477Met); silent changes which did not change the encoded amino acid (Leu-30Leu; Pro35Pro; Ile303Ile, Gly418Gly); and those that do not cose-gregate with the protein S deficiency (5'UT TC exon 1-286; intron a, AG, exon 1 +7; intron a, del ATT, exon 2 −7; intron b, GA, exon 2 +5; intron g, GA, exon 8 −20, Arg49His, Thr57Ser, Met344Val, Ile518Met). Variation at one of the three glycosylation sites N-X-SIT (Ser460Pro) results in loss of the sugar modification, but no functional consequence of this change has been unequivocally demonstrated.

An electronic database is available of more than 100 different mutations and polymorphisms of human protein S (see Gandrille et al. *Thromb. Haemost.* 77:1201-1214, 1997). It is preferred that the protein S or functional variant thereof be derived from the same species as the organism being treated.

"Protein S" refers to native genes and proteins belonging to this family as well as variants thereof (e.g., mutations and polymorphisms found in nature or artificially designed). The chemical structure of the genes and proteins may be a polymer of natural or non-natural nucleotides connected by natural or non-natural covalent linkages (i.e., polynucleotide) or a polymer of natural or non-natural amino acids connected by natural or non-natural covalent linkages (i.e., poly-peptide). See Tables 1-4 of WIPO Standard ST.25 (1998) for a nonlimiting list of natural and non-natural nucleotides and amino acids. See Tables 1-4 of WIPO Standard ST.25 (1998) for a nonlimiting list of natural and non-natural nucleotides and amino acids. Protein S genes and proteins may be recognized as belonging to this family by comparison to the human homologs PROS1 and PROS2, use of nucleic acid binding (e.g., stringent hybridization conditions of 400 mM NaCl, 40 mM PIPES pH 6.4, 1 mM EDTA, at 50° C. or 70° C. for an oligonucleotide; 500 mM NaHPO$_4$ pH 7.2, 7% SDS, 1% BSA, 1 mM EDTA, at 45° C. or 65° C. for a polynucleotide of 50 bases or longer; and appropriate washing) or protein binding (e.g., specific immunoassay under stringent binding conditions of 50 mM Tris-HCl pH 7.4, 500 mM NaCl, 0.05% TWEEN 20 surfactant, 1% BSA, at room temperature and appropriate washing); or computer algorithms (Doolittle, *Of URFS and ORFS*, 1986; Gribskov & Devereux, *Sequence Analysis Primer*, 1991; and references cited therein). For example, washing may be initiated at an ionic strength, pH, and temperature equivalent to the hybridization/binding conditions (with or without blocking agents and/or surfactants), then decreasing the salt concentration or increasing the temperature with one or more changes of washing solution until the desired degree of specificity is achieved.

A "mutation" refers to one or more changes in the sequence of poly-nucleotides and polypeptides as compared to native protein S, and has at least one function that is more active or less active, an existing function that is changed or absent, a novel function that is not naturally present, or combinations thereof. In contrast, a "polymorphism" also refers to a difference in its sequence as compared to native protein S, but the changes do not necessarily have functional consequences. Mutations and polymorphisms can be made by genetic engineering or chemical synthesis, but the latter is preferred for non-natural nucleotides, amino acids, or linkages. Fusions of domains linked in their reading frames are another way of generating diversity in sequence or mixing-and-matching functional domains. For example, homologous protein C and protein S work best together and this indicates that their sequences may have coevolved to optimize interactions between the enzyme and its cofactor. Exon shuffling or gene shuffling techniques may be used to select desirable phenotypes in a chosen background (e.g., combining sequence changes that confer loss of glycosylation at Asn458 and APC cofactor activity, hybrid human/mouse sequences which locate the species determinants).

Percentage identity between a pair of sequences may be calculated by the algorithm implemented in the BESTFIT computer program (Smith & Waterman. *J. Mol. Biol.* 147: 195-197,1981; Pearson, *Genomics* 11:635-650,1991). Another algorithm that calculates sequence divergence has been adapted for rapid database searching and implemented in the BLAST computer program (Altschul et al., *Nucl. Acids Res.* 25:3389-3402, 1997). In comparison to the human sequence, the protein S polynucleotide or polypeptide may be only about 60% identical at the amino acid level (protein S from different mammals are only about 59% identical), 70% or more identical, 80% or more identical, 90% or more identical, or greater than 95% identical.

Conservative amino acid substitutions (e.g., Glu/Asp, Val/Ile, Ser/Thr, Arg/Lys, Gln/Asn) may also be considered when making comparisons because the chemical similarity of these pairs of amino acid residues are expected to result in functional equivalency in many cases. Amino acid substitutions that are expected to conserve the biological function of the polypeptide would conserve chemical attributes of the substituted amino acid residues such as hydrophobicity, hydrophilicity, sidechain charge, or size. Functional equivalency or conservation of biological function may be evaluated by methods for structural determination and bioassay.

The codons used may also be adapted for translation in a heterologous host by adopting the codon preferences of the host. This would accommodate the translational machinery of the heterologous host without a substantial change in chemical structure of the polypeptide. For example, a mammalian protein S or variant thereof may have its codons altered for translation in a bacterial or fungal host.

Protein S and variants thereof (i.e., deletion, domain shuffling or duplication, insertion, substitution, or combinations thereof) may be used to determine structure-function relationships (e.g., alanine scanning, conservative or nonconservative amino acid substitution). For example, protein S folding and processing, protein S secretion, protein S binding to phospholipids and other proteins, any of the biological activities described herein, or combinations thereof may be related to changes in the amino acid sequence. See Wells (*Bio/Technology* 13:647651, 1995) and U.S. Pat. No. 5,534,617. Directed evolution by directed or random mutagenesis or gene shuffling using protein S may be used to acquire new and improved functions in accordance with selection criteria. Mutant and polymorphic variant polypeptides are encoded by suitable mutant and polymorphic variant polynucleotides. Structure-activity relationships of protein S may be studied (i.e., SAR studies) using variant polypeptides produced with an expression construct transfected in a host cell with or without expressing endogenous protein S. Thus, mutations in discrete domains of protein S may be associated with decreasing or even increasing activity in the protein's function.

Formulations and Their Administration

Protein S or variants thereof may be used to formulate pharmaceutical compositions with one or more of the utilities disclosed herein. They may be administered in vitro to cells in culture, in vivo to cells in the body, or ex vivo to cells outside of a subject which may then be returned to the body of the same subject or another. The cells may be removed from, transplanted into, or be present in the subject.

Use of compositions which further comprise a pharmaceutically acceptable carrier and compositions which further comprise components useful for delivering the composition to a subject's brain are known in the art. Addition of such carriers and other components to the composition of the invention is well within the level of skill in this art.

A pharmaceutical composition may be administered as a formulation which is adapted for direct application to the central nervous system, or suitable for passage through the gut or blood circulation. Alternatively, pharmaceutical compositions may be added to the culture medium. In addition to active compound, such compositions may contain pharmaceutically-acceptable carriers and other ingredients known to facilitate administration and/or enhance uptake. It may be administered in a single dose or in multiple doses which are administered at different times.

Pharmaceutical compositions may be administered by any known route. By way of example, the composition may be administered by a mucosal, pulmonary, topical, or other localized or systemic route (e.g., parenteral). "Parenteral" includes subcutaneous, intradermal, intramuscular, intravenous, intra-arterial, intrathecal, and other injection or infusion techniques, without limitation. In particular, achieving an effective amount of protein S in the central or peripheral nervous system may be desired. This may involve a depot injection into or surgical implant within the brain. Intravenous administration may be used for stroke and intra-arterial administration may be used during neurosurgery.

Suitable choices in amounts and timing of doses, formulation, and routes of administration can be made with the goals of achieving a favorable response in the subject (i.e., efficacy), and avoiding undue toxicity or other harm thereto (i.e., safety). Therefore, "effective" refers to such choices that involve routine manipulation of conditions to achieve a desired effect (e.g., neuroprotection; anti-thrombotic activity; anti-inflammatory activity; inhibition of apoptosis; or preventing the injury caused by ischemia, hypoxia, re-oxygentation, or the like).

A bolus of the formulation administered only once to a subject is a convenient dosing schedule although achieving an effective concentration of protein S in the brain may require more frequent administration. Alternatively, an effective dose may be administered every other day, once a week, or once a month. Dosage levels of active ingredients in a pharmaceutical composition can also be varied so as to achieve a transient or sustained concentration of the compound or derivative thereof in a subject and to result in the desired therapeutic response. But it is also within the skill of the art to start doses at levels lower than required to achieve the desired therapeutic effect and to gradually increase the dosage until the desired effect is achieved.

The amount of compound administered is dependent upon factors such as, for example, bioactivity and bioavailability of the compound (e.g., half-life in the body, stability, and metabolism); chemical properties of the compound (e.g., molecular weight, hydrophobicity, and solubility); route and scheduling of administration; and the like. It will also be understood that the specific dose level to be achieved for any particular subject may depend on a variety of factors, including age, health, medical history, weight, combination with one or more other drugs, and severity of disease.

The term "treatment" refers to, inter alia, reducing or alleviating one or more symptoms of disease or another pathological condition in a subject. This includes therapy of an affected subject or prophylaxis of a subject at risk. For a given subject, improvement in a symptom, its worsening, regression, or progression may be determined by an objective or subjective measure. Treatment may also involve combination with other existing modes of treatment and agents (e.g., protein C, activated protein C, other anti-thrombotic agents, steroidal or nonsteroidal anti-inflammatory agents). Thus, combination treatment may be practiced.

EXAMPLES

The effects of purified human plasma-derived or recombinant protein S was examined in a murine in vivo model of focal ischemic stroke and an in vitro neuronal hypoxic/re-oxygenation injury. Protein S significantly improved motor neurological function after stroke and reduced brain infarction and edema in a dose-dependent manner. At higher concentrations protein S enhanced post-ischemic reperfusion and reduced brain fibrin and neutrophils deposition. In vitro protein S protected cultured cortical neurons from hypoxia/re-oxygenation-induced apoptosis. Protein S may be a prototype of a new class of neuroprotective agents with combined anti-thrombotic, anti-inflammatory and direct cellular neuroprotective effects to treat disease associated with ischemia, hypoxia, and other re-oxygenation injury (e.g., stroke) as well as similar diseases and other pathological conditions.

Animals. Procedures were approved by the University of Rochester's Institutional Animal Care and Use Committee. Male C57BL/6 mice (23-26 gm) were anesthetized with an intraperitoneal injection of ketamine (100 mg/kg) and xylazine (10 mg/kg). Animals were allowed to breath spontaneously. Rectal temperature was maintained at 37° C.±1° C. Their right femoral arteries were cannulated for monitoring of blood pressure and blood analysis.

Stroke model. A modification of the intravascular, middle cerebral artery (MCA) occlusion technique (33,34) was used to induce stroke. A non-siliconized non-coated 6-10 mm±1 mm long prolene suture with a rounded tip (diameter 0.20 mm) was advanced into the internal carotid artery to occlude the MCA for 1 hr followed by 23 hr of reperfusion.

Protein S, human plasma-derived (0.2, 0.5 or 2 mg/kg), human recombinant protein S (2 mg/kg) or vehicle were administered intravenously 10 min after the MCA occlusion (n=6 per group). Protein S was purified as previously described (4).

Protein S was given at 10 min after the induction of stroke when blood flow was at a minimum to give a reasonable test of the bioactivity of protein S during ischemia in the murine model (33). In this regard, we note that the time course of pathophysiological changes in the present model is different from human strokes and the occlusion in this model is removed after one hour. Moreover, in the clinical situation in humans, spontaneous reopening of major occluded blood vessels in patients with ischemic stroke does not typically happen within one hour after the insult (27).

Cerebral blood flow (CBF) was monitored by Laser Doppler Flowmetry (LDF, Transonic Systems) (33,34). LDF probes (0.8 mm diameter) were positioned on the cortical surface 2 mm posterior to the bregma, both 3 mm and 6 mm to each side of midline. The procedure was considered successful if ≧80% drop in CBF was observed immediately after placement of the suture. Head temperature was monitored with a 36-gauge thermocouple probe in the temporalis muscle (Model 9000, Omega, Conn.).

Neurologic examinations were performed at 24 hr and scored (33): no neurologic deficit 0, failure to fully extend left forepaw 1, turning to left 2, circling to left 3, unable to walk spontaneously 4, and stroke-related death 5.

Arterial blood gases (pH, $PaO_2$, $PaCO_2$) were measured before and during MCA occlusion using ABL 30 Acid-Base Analyzer (Radiometer).

Unfixed 1 mm coronal brain slices were incubated in 2% TTC in phosphate buffer (pH 7.4). Serial coronal sections were displayed on a digitizing video screen (Jandel Scientific). Brain infarction and edema volume were calculated using Swanson correction (33,34).

Histopathology and fibrin detection. Leukocytes were stained using anti-CD11b antibody (DAKO) (1:250 dilution) directed against leukocyte Mac-1 (33). The number of CD11b positive cells in tissue was given per $mm^2$. Previous study has demonstrated that the number of CD11b positive cells and dichloracetate esterase (a specific marker for neutrophils) positive cells in the murine model of stroke is identical (33). Counting was performed in ten random fields in the ischemic hemisphere by two independent observers blinded to the specimen source or timing. Routine controls included deletion of primary antibody, deletion of secondary antibody and/or the use of an irrelevant primary antibody. The amount of fibrin was quantified in 1 mm thick brain hemisections by Western blotting using anti-fibrin II antibody (NYB-T2G1, Accurate Chemical) (1:500 dilution) as described (33,34).

Protein S ELISA Assay. The amount of human protein S in plasma of mice at 1 hr after they received protein S injections (0.2, 0.5, 2.0 or 6.0 mg/kg) was quantitated by ELISA as follows. Nunc Maxisorp microplates were coated with 20 μg/ml of polyclonal rabbit purified IgG anti-protein S (DAKO Corp.) in 0.1 M Na carbonate, pH 9.0 (150 μl/well) overnight at 10° C. and then blocked with 200 μl buffer/well containing 50 mM Tris 100 mM NaCl, pH 7.4, 2% BSA for 2 hr. Aliquots (150 μl) of plasma diluted 1/400 and 1/1600 in 50 mM Tris, 100 mM NaCl, 0.02% Tween-20, 0.5% BSA were added to wells and incubated for 2 hr. Following washing with TBS, 0.02% Tween-20, polyclonal HRP-labeled rabbit antibody (5 μg/ml, DAKO) was used with OPD substrate (Sigma Chemical) to detect bound protein S. Standard curves, valid for 5 to 125 ng/ml protein S, were made with dilutions (1/200 to 1/6400) of pooled normal human plasma (assumed to contain 25 μg/ml protein S, George King Inc.). A plasma pool from 10 normal male mice gave no signal in this assay whereas the same plasma containing purified human protein S (final concentration of 25 μg/ml) gave a standard curve indistinguishable from pooled human plasma.

Cell Culture. Primary neuronal cortical cultures were established as described (35). In brief, cerebral cortex was dissected from fetal C56BL/6 mice at 16 days of gestation, treated with trypsin for 10 min at 37° C. and dissociated by trituration. Dissociated cell suspensions were plated at $5\times10^5$ cells per well on 12-well corning tissue culture dishes coated with poly-D-lysine, in serum-free Neurobasal medium plus B27 supplement (GIBCO BRL). The absence of astrocytes was confirmed by negative staining for the glial fibrillary acidic protein. Cultures were maintained in a humidified 5% $CO_2$ incubator at 37° C. for 5 days before treatment. To induce hypoxic re-oxygenation injury, five-day-old cultures were treated first for 12 hr with 95% $N_2$/5% $CO_2$ in DMEM serum-free medium without glucose, and next for 12 hr exposed to normoxic conditions and medium containing 5 mM glucose (36). Protein S, human plasma-derived (1 nM to 1,000 nM) protein S, or recombinant protein S was added to the medium throughout the entire 24 hr of the study. Cultures were next fixed for 10 min with 4% formaldehyde in PBS at 4° C. and double stained with Hoechst 33258 (1 μg/ml) and TUNEL (terminal-deoxynucleotidyl-transferase-mediated dUTP nick-end labeling) to determine nuclear morphological changes and the number of apoptotic cells.

Oxidative Stress Model. Human microvascular brain endothelial cells (MBEC) were isolated by biopsy and cultured using methods similar to those previously reported by Mackic et al. (*J. Clin. Invest.* 102:734-743, 1998). Briefly, brain tissue was cut into small pieces, and then mechanically dissociated using a loose-fitting cell homogenizer in RPMI 1640 with 2% fetal calf serum (FCS) and penicillin/streptomycin. The homogenate was then fractionated over 15% dextran by centrifugation at 10,000 g for 10 min to obtain a brain microvessel pellet. Microvessels were further digested with 1 mg/ml of collagenase/dispase and 5 μl/ml of DNase in FCS-enriched medium for 1 hr at 37° C. This cell suspension was centrifuged at 1000 g for 5 min, and the cell pellet was plated on fibronectin-coated flasks in RPMI 1640 with 10% FCS, 10% NuSerum, endothelial cell growth factors, nonessential amino acids, vitamins, and penicillin/streptomycin as a primary culture.

The P0 primary cultures were grown to confluence, and sorted based on LDL binding using the Dil-Ac-LDL method following the manufacturer's instructions (Biomedical Technology). Briefly, cells were incubated with Dil-Ac-LDL ligand for 4 hr at 37° C., trypsinized, and then separated by fluorescence activated cell sorting (FACS). Labeled and unlabeled human umbilical vein endothelial cells (HUVEC) were used to set gating limits as positive and negative controls, respectively. Unlabeled MBEC were used to control for possible background staining or differences based on cell size. Positively sorted cells were plated on fibronectin- or collagen-coated flasks in the medium described above. Cultures were grown in 5% $CO_2$ and split 1:3 at confluency with collagenase/dispase.

Subconfluent brain endothelial cell cultures (3-4 days after subculture) were treated with $H_2O_2$ by adding it to the culture medium for 2 hr. To induce senescence sublethal doses of $H_2O_2$ were determined and selected. After treatment the cells were washed with PBS (37° C.) before harvesting, subculturing, or incubating with a fresh medium or 3-D collagen gels.

Statistics. Physiological variables, injury, infarction and edema volumes were compared using ANOVA followed by Dunnett's multiple comparisons test with the control group or Student's t-test when two groups were compared. Non-parametric data (neurologic outcome scores) was subjected to the Chi-squared test with Fisher's transformation.

Animals treated with protein S had no significant differences in mean arterial blood pressure, $PaO_2$, $PaCO_2$, pH, hematocrit, head temperature, and blood glucose when compared with control animals. Protein S administration did not influence CBF under basal conditions. During MCA occlusion, the CBF in the control group dropped to 17-18% of baseline (p<0.001); treatment with protein S (0.2 mg/kg to 2 mg/kg) did not improve the CBF during the occlusion phase (FIG. 1, Table 1). During post-ischemic reperfusion, the CBF returned to 58-52% of baseline in the control group (FIG. 1A, Table 1). Protein S at 2 mg/kg significantly improved the CBF during post-ischemic reperfusion by 21% to 26% (p<0.05; Table 1), but the effects of the lower doses of protein S were either marginal or lacking (see Table 1).

TABLE 1

CBF after MCA occlusion (60 min) followed by reperfusion.

| Treatment | Occlusion | | Reperfusion | |
| --- | --- | --- | --- | --- |
| | 0-30 min | 30-60 min | 0-30 min | 30-60 min |
| Vehicle | 17.5 + 2.5 | 17.7 + 1.8 | 58.2 + 3.8 | 52.1 + 2.9 |
| Protein S | | | | |
| 2.0 mg/kg | 17.9 + 1.5 | 16.8 + 1.3 | 70.6 + 2.5* | 65.8 + 3.4* |
| 0.5 mg/kg | 16.0 + 2.1 | 16.9 + 3.2 | 65.7 + 1.6* | 58.5 + 3.3 |
| 0.2 mg/kg | 15.3 + 3.5 | 16.0 + 2.3 | 60.1 + 4.7 | 59.7 + 4.9 |

CBF during MCA occlusion/reperfusion in control and protein S-treated mice. Vehicle or protein S were given 10 min after initiation of MCA occlusion. CBF values (mean+SD) were averaged over studied period at time of occlusion or reperfusion and expressed as a percentage of baseline. *p<0.05

Control mice developed significant motor neurological deficit with a score close to 4 (Table 2). At the lowest dose (0.2 mg/kg), protein S reduced motor deficit and improved the average score by 1.4-fold, while at higher doses at 0.5 mg/kg and 2 mg/kg protein S improved significantly the motor score by 3.2-fold (Table 1).

TABLE 2

Motor neurological scores at 24 hr after MCA occlusion/reperfusion.

| Treatment | No. of mice With score of | | | | | | Score |
| --- | --- | --- | --- | --- | --- | --- | --- |
| | 0 | 1 | 2 | 3 | 4 | 5 | (mean ± SE) |
| Vehicle | 0 | 0 | 0 | 1 | 5 | 0 | 3.83 ± 0.17 |
| Plasma-derived | | | | | | | |
| Protein S | | | | | | | |
| 2.0 mg/kg | 3 | 1 | 1 | 0 | 1 | 0 | 1.17 ± 0.65* |
| 0.5 mg/kg | 3 | 1 | 1 | 0 | 1 | 0 | 1.17 ± 0.65* |
| 0.2 mg/kg | 3 | 1 | 0 | 0 | 1 | 0 | 1.00 ± 0.77* |

Protein S or vehicle were administered 10 min after stroke induction. *p<0.05 by Kruskal-Wallis test.

Protein S-treated animals were sacrificed at 24 hr to determine the volume of brain injury. Protein S significantly reduced brain injury volume and edema volume in a dose-dependent manner by 35% and 43% at 0.2 mg/kg (p<0.05), respectively, and by 59% and 62% at 2 mg/kg (p<0.01), respectively (FIGS. 2A and 2B). As shown for example in FIG. 2C, the infarction area was significantly reduced in four out of the seven coronal sections with 0.5 mg/kg of protein S. All control mice had significant injury in the cortex and striatum on the side of the occlusion (FIG. 3); ≧50% of mice exhibited changes in the medial striatum while <50% had changes in the dorsomedial and ventromedial cortex (FIG. 3A). Protein S (2 mg/kg) limited brain injury to a small well-localized area in the striatum and spared most of the brain (FIG. 3B). Similar effects were obtained with recombinant protein S.

At 2 mg/kg, protein S reduced the amount of deposited fibrin in the ischemic hemisphere by 40% (p<0.05; FIGS. 4A and 4B) and the number of CD11 b-positive leukocytes by 53% (p<0.01; FIG. 4C).

To quantitate the circulating protein S levels in these studies, four mice were each injected with each dose of protein S. Blood samples were obtained an hour later and levels of human protein S in mouse plasma were determined using an ELISA. The mean levels of circulating human protein S were 4.9, 11.0, 51.8 or 155 µg/ml for injections of 0.2, 0.5, 2.0 or 6.0 mg/kg, respectively.

The direct effects of protein S in vitro on cultured mouse cortical neurons were studied. Neurons cultured under normoxic conditions exhibited occasionally TUNEL-positive staining and chromatin condensation (FIG. 5A, left panels). In contrast, during ischemic hypoxia/re-oxygenation injury, most of the cultured neurons were TUNEL-positive and exhibited nuclear condensation and/or fragmentation (FIG. 5B, middle panels). In the presence of protein S there was approximately 70% reduction (p<0.05) in the number of apoptotic cells (FIG. 5A, right panels and FIG. 5B). Under the present experimental conditions, protection of neurons from apoptotic death by protein S was time-dependent and dose-dependent with the half-maximal effect $EC_{50}$ at 75 nM (FIGS. 5C-5D).

Neuroprotective effects of plasma-derived human protein S on primary human microvascular brain endothelial cells (MBEC) obtained from biopsies and exposed to 500 µM $H_2O_2$ for 1.5 hr. In this oxidative stress model, about 50-70% of cells became apoptotic as shown by TUNEL and Hoechst staining. Protein S administered two hours prior to oxidative stress reduced the number of TUNEL-positive cells in a dose-dependent manner with an $EC_{50}$ of 200 nM. Next, it was demonstrated that IgG anti-annexin II (2.5 µg/ml) and IgG anti-Tyro3 (2.0 µg/ml) inhibit by >95% the anti-apoptotic effects of protein S. These findings indicate that protein S acts as a cell survival factor in brain endothelium exposed to oxidative damage, and that annexin II and Tyro3 are required for its anti-apoptotic effects.

Data presented have demonstrated neuroprotective, anti-thrombotic, and anti-inflammatory effects of protein S in a murine in vivo model of focal ischemic stroke with reperfusion and direct neuronal protective effects of protein S in an in vitro model of ischemia using murine cultured cortical neurons challenged by hypoxialaglycemia followed by re-oxygenation. In the stroke model, protein S reduced the motor neurological deficit, the infarction volume and the edema volume in a dose-dependent manner. The effect of protein S on post-ischemic CBF during reperfusion was significant with 2 mg/kg, but marginal with an intermediate dose (0.5 mg/kg) and/or absent with a low 0.2 mg/kg dose. It is noteworthy that the same low dose of protein S (0.2 mg/kg) significantly reduced the injury and edema volumes by 35% and 43%, respectively, in spite of the lack of an observable effect on CBF.

We studied protein S in a murine in vivo model of stroke and an in vitro model of neuronal hypoxic/re-oxygenation injury. Animals received purified human plasma-derived protein S or vehicle intravenously 10 min after initiation of middle cerebral artery occlusion followed by reperfusion. Protein S at 0.2 to 2 mg/kg significantly improved the motor neurological deficit by 1.4- to 3.2-fold and reduced infarction volume by 35 to 59% and brain edema by 45 to 62% in a dose-dependent manner. Protein S at 2 mg/kg improved the post-ischemic cerebral blood flow by 21% to 26% and reduced brain fibrin deposition and infiltration with neutrophils by 40% and 53%, respectively. Intracerebral bleeding was not observed with protein S. Protein S protected cultured neurons from hypoxia/re-oxygenation-induced apoptosis in a dose-dependent manner. Recombinant human protein S exerted similar protective effects from hypoxia-induced damage as the plasma-derived protein S both in vivo and in vitro.

Significant obstructions in CBF in focal stroke might result from microvascular occlusions due to fibrin deposition, vascular accumulation of neutrophils and brain swelling (33,34).

Previous studies reported significant anticoagulant activity of protein S in vitro and in vivo (2-7,28). The present study confirmed reduced fibrin deposition and reduced infiltration of brain tissue with leukocytes in the presence of protein S. Protein S alleviated ischemic cerebral coagulopathy and reduced ischemic microvascular obstructions with blood cells, thereby limiting the development of brain thrombosis and contributing to the restoration of post-ischemic brain perfusion. However, the cerebroprotective effects were also observed with the lower doses of protein S, which apparently did not affect and/or improve significantly the post-ischemic CBF. Therefore, in addition to anti-thrombotic mechanisms of protein S during brain ischemia, we also considered other possible mechanisms including direct neuroprotective cellular effects.

Remarkably, our studies also demonstrated that protein S directly protects ischemic cultured neurons exposed to hypoxic/re-oxygenation injury in vitro. In the presence of protein S the number of cultured neurons that were TUNEL-positive and exhibiting nuclear shrinkage, chromatin condensation and nuclear fragmentation were significantly reduced in a dose-dependent manner. Under these conditions, protein S was able to spare about 70% of neurons with an $EC_{50}$ of 75 nM. Cell binding and mitogenic effects of protein S have been demonstrated in vascular smooth muscle cells (18-20), while the anti-apoptotic effects of gas6, a structural homolog of protein S, are well established (22-24). The molecular nature of a protein S receptor as a transmembrane tyrosine kinase receptor has been debated (25,26). Direct anti-apoptotic activity of protein S has not been previously described. Some studies have suggested that both gas6 and protein S are ligands for the Tyro3/Axl family of receptor tyrosine kinases (25). However, the role of Tyro3/Axl receptors has not been confirmed by others (20,26) and the nature of the receptor for protein S on neuronal cells was unknown. It has been also suggested that mitogen activated protein kinases (MAPK) $p_{42}/p_{44}^{MARK}$ mediate protein S membrane to nuclear signaling that might be involved in cell proliferation in vascular smooth muscle cells (20). Similar intracellular signaling may mediate the cytoprotective and/or neuroprotective effects of protein S.

Bleeding and intracerebral hemorrhage are potential life-hreatening complications with anti-thrombotic therapy for stroke including thrombolytic treatment with tPA (29) or anticoagulant treatment with heparin (27). In addition, tPA is directly toxic for brain cells (30,31) in contrast to cellular neuropro-tection conferred by protein S. This study indicated that protein S does not adversely affect hemostatic function or produce intracerebral hemorrhage, consistent with previous studies demonstrating that administration of protein S does not cause bleeding (28). Thus, protein S and variants thereof serve as prototypes of a new class of agents for clinical stroke with combined systemic anti-thrombotic and anti-inflammatory activities as well as direct protective effects on neurons during cerebral ischemia.

REFERENCES

1. Griffin Chapter 113. Regulation of Coagulation. In: *William's Hematology* $6^{th}$ *Edition* pp. 1435-1449 (2000).
2. Heeb et al. Binding of protein S to factor Va associated with inhibition of prothrombinase that is independent of activated protein C. *J. Biol. Chem.* 268:2872-2877 (1993).
3. Hackeng et al. Human protein S inhibits prothrombinase complex activity on endothelial cells and platelets via direct interactions with factors Va and Xa. *J Biol Chem* 269:21051-21058 (1994).
4. Heeb et al. Protein S binds to and inhibits factor Xa. *Proc. Natl. Acad. Sci. USA* 91:2728-2732 (1994).
5. Koedam et al. Inactivation of human factor VIII by activated protein C. Cofactor activity of protein S and protective effect of von Willebrand factor. *J. Clin. Invest.* 82:1236-1243 (1988).
6. Rosing et al. Effects of protein S and factor Xa on peptide bond cleavages during inactivation of factor Va and factor VaR506Q by activated protein C. *J. Biol. Chem.* 270: 27852-27858 (1995).
7. Lu et al. Comparison of activated protein C/protein S-mediated inactivation of human factor VIII and factor V. *Blood* 87:4708-4717 (1996).
8. Mahasandena et al. Clinical and laboratory observations: homozygous protein S deficiency in an infant with purpora fulmainans. *J. Pediatrics* 117:750-753 (1990).
9. Pegelow et al. Severe protein S deficiency in a newborn. *Pediatrics* 89:674-676(1992).
10. Schwarz et al. Plasma protein S deficiency in familial thrombotic disease. *Blood* 64:1297-1300 (1984).
11. Comp et al. Familial protein S deficiency is associated with recurrent thrombosis. *J. Clin. Invest.* 74:2082-2088 (1984).
12. Comp & Esmon. Recurrent venous thromboembolism in patients with a partial deficiency of protein S. *New Engl. J. Med.* 311:1525-1528 (1984).
13. Gladson et al. The frequency of type 1 heterozygous protein S and protein C deficiency in 141 unrelated young patients with venous thrombosis. *Thromb. Haemost.* 59:18-22 (1988).
14. Green et al. Protein S deficiency in middle aged women with stroke. *Neurology* 42:1029-1033 (1992).
15. Koller et al. Deficiency of both protein C and protein S in a family with ischemic strokes in young adults. *Neurology* 44:1238-1240 (1994).
16. Prats et al. Superior sagital sinus thrombosis in a child with protein S deficiency. *Neurology* 42:2303-2305 (1992).
17. Bostroem et al. Thrombophlébite cérébrale, phlébite surale, embolies pulmonaires et déficits en protéine *S. Rev. Neurol.* (Paris) 152:755-758 (1996).
18. Gasic et al. Coagulation factors X, Xa and protein S, as potent mitogens of cultured aortic smooth muscle cells. *Proc. Natl. Acad. Sci. USA* 89:2317-2324 (1992).
19. Benzakour et al. Evidence for a protein S receptor(s) on human vascular smooth muscle cells. Analysis of the binding characteristics and mitogenic properties of protein S on human vascular smooth muscle cells. *Biochem. J.* 308:481-485.(1995).
20. Kanthou & Benzakour. Cellular effects and signaling pathways activated by the anti-coagulant factor, protein S, in vascular cells. Protein S cellular effects. In: *Angiogenesis: From the Molecular to Integrative Pharmacology* pp. 155-166 (2000).
21. Schneider et al. Genes specifically expressed at growth arrest of mammalian cells. *Cell* 54:787-793 (1988).
22. Bellosta et al. Signaling through the ARK tyrosine kinase receptor protects from apoptosis in the absence of growth stimulation. *Oncogene* 15:2387-2397 (1997).
23. Goruppi et al. Gas6, the ligand of Axl tyrosine kinase receptor, has mitogenic and survival activities for serum starved NIH-3T3 fibroblasts. *Oncogene* 12:471-480 (1996).
24. Nakano et al. Prevention of growth arrest-induced cell death of vascular smooth muscle cells by a product of growth arrest-specific gene, gas6. *FEBS Lett.* 387:78-80 (1996).

25. Stitt et al. The anticoagulation factor protein S and its relative, gas6, are ligands for the tyro 3/axl family of receptor tyrosine kinases. *Cell* 80:661-670 (1995).
26. Godowski et al. Reevaluation of the roles of protein S and gas6 as ligands for the receptor tyrosine kinase rse/tyro 3. *Cell* 82:355-358 (1995).
27. Zivin. Factors determining the therapeutic window for stroke. *Neurology* 50:599-603 (1998).
28. Arnljots & Dahlback. Antithrombotic effects of activated protein C and protein S in a rabbit model of microarterial thrombosis. *Arterioscler. Thromb. Vasc. Biol.* 15:937-941 (1995).
29. del Zoppo et al. Hemorrhagic transformation following tissue plasminogen activator in experimental cerebral infarction. *Stroke* 21:596-601 (1990).
30. Wang et al. Tissue plasminogen activator (tPA) increases neuronal damage after focal cerebral ischemia in wild-type and tPA-deficient mice. *Nature Med.* 2:228-231 (1998).
31. Flavin et al. Microglial tissue plasminogen activator (tPA) triggers neuronal apoptosis in vitro. *Glia* 29:347-354 (2000).
32. Goodnight & Griffin. Chapter 127. Hereditary Thrombophilia. In: *William's Hematology 6th Edition* pp. 1697-1714 (2000).
33. Shibata et al. Anti-inflammatory, antithrombotic, and neuroprotective effects of activated protein C in a murine model of focal ischemic stroke. *Circulation* 103:1799-805 (2001).
34. Tabrizi et al. Tissue plasminogen activator (tPA) deficiency exacerbates cerebrovascular fibrin deposition and brain injury in a murine stroke model. *Arterioscler. Thromb. Vasc. Biol.* 19:2801-2806 (1999).
35. Xiang et al. Evidence for p53-mediated modulation of neuronal viability. *J. Neuro. Sci.* 16:6753-6756 (1996).
36. Koretz et al. Pre- and post-synaptic modulators of excitatory neurotransmission: comparative effects of hypoxia/hypoglycemia in cortical cultures. *Brain Res.* 643:334-337 (1994).
37. del Zoppo. Microvascular response to cerebral ischemia/inflammation. *Ann. NY Acad. Sci.* 823:132-147 (1997).

Patents, patent applications, books, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of these transitions can be used to claim the invention.

It should be understood that an element described in this specification should not be construed as a limitation of the claimed invention unless it is explicitly recited in the claims. For example, functional variants of protein S are known as homologs, mutations, and polymorphisms in the human nucleotide and amino acid sequences. In addition, Gas6 analogs and/or receptor agonists (e.g., ligands) of annexin II or members of the Tyro3/Axl family may be used as functional equivalents of protein S and its functional variants. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention. For example, neuroprotection may be manifested by inhibition of apoptosis, promotion of cell survival, prevention of neuronal injury and/or cell death, and other general cytoprotective effects.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A method of protecting one or more cell types of a human subject's nervous system, comprising
   administering to a human subject an amount of human protein S effective to provide neuroprotection,
   wherein no protein C or activated protein C is administered,
   and wherein the human subject has a brain injury caused by cerebral ischemia, cerebral hypoxia, cerebral re-oxygenation or any combination thereof.

2. The method of claim 1, wherein there is no deficiency of protein S activity in the human subject.

3. The method of claim 1, wherein the protein S polypeptide is administered before and/or after diagnosis of disease or another pathological condition.

4. The method of claim 1, wherein cerebral blood flow in the human subject's brain is increased by administration of the protein S polypeptide.

5. The method of claim 1, wherein volume of the human subject's brain which is affected by injury, infarction, edema, or a combination thereof is decreased by administration of the protein S polypeptide.

6. A method of treating stroke in a human subject, comprising
   administering to a human subject an amount of human protein S effective to treat stroke,
   wherein no protein C or activated protein C is administered,
   and wherein the human subject has experienced stroke.

7. The method of claim 6, wherein there is no deficiency of protein S activity in the human subject.

8. The method of claim 6, wherein cerebral blood flow in the human subject's brain is increased by administration of the protein S polypeptide.

9. The method of claim 6, wherein volume of the human subject's brain which is affected by stroke is decreased by administration of the protein S polypeptide.

* * * * *